United States Patent [19]

Kravitz

[11] 4,008,605
[45] Feb. 22, 1977

[54] IMPACT TEST METHOD
[75] Inventor: Rubin Kravitz, Worcester, Mass.
[73] Assignee: Foster Grant Co., Inc., Leominster, Mass.
[22] Filed: Jan. 21, 1976
[21] Appl. No.: 651,326
[52] U.S. Cl. .................................................. 73/101
[51] Int. Cl.² ........................................ G01N 3/30
[58] Field of Search ...................... 73/101, 12, 103
[56] References Cited
UNITED STATES PATENTS

| | | | |
|---|---|---|---|
| 2,617,293 | 11/1952 | Schnadt | 73/101 |
| 3,209,585 | 10/1965 | Wolstenholme et al. | 73/101 |

*Primary Examiner*—Jerry W. Myracle
*Attorney, Agent, or Firm*—Michael J. Tully

[57] ABSTRACT

A quick and reproducible method is disclosed for evaluating the impact properties of relatively stiff materials such as plastic. A test specimen in the form of a thin unnotched strand of known thickness is mounted in a holding means and subjected to impact by a pendulum type striking means having a predetermined potential energy content. The excess energy remaining in the striking means after breaking the specimen is measured and impact values determined by a mathematical formula as a function of specimen thickness and energy required to break the specimen.

9 Claims, 2 Drawing Figures

IMPACT TEST METHOD

BACKGROUND OF THE INVENTION

The present invention relates to a novel and simple method for evaluating a physical property of relatively hard, stiff materials such as plastics. More specifically, a simplified method is disclosed wherein the resistance of materials to breaking under sudden impact is measured.

Various methods and apparatus have been devised over the years for measuring the mechanical properties of relatively stiff materials. In the plastics industry it is of critical importance to both the manufacturer and the user of plastics to have at their disposal simple and reliable test methods for measuring the response of plastic materials to certain stresses such as tension, shear, bending, impact and the like. The fabricator of finished goods in particular must be able to quickly perform tests on the various raw material plastics used by him to insure that these materials meet minimum performance specifications.

Measurement of resistance to impact is of critical importance in obtaining a physical property profile of a given material, and numerous tests have been devised to perform such measurement. For example, U.S. Pat. No. 403,676, issued in 1889, teaches a pendulum type device comprising a support, a swinging hammer and a scale whereby the force required to break a mounted test bar sample can be measured. U.S. Pat. No. 1,462,813 discloses a different variation of the same idea whereby a hammer is pivotally mounted and caused to drop upon a test specimen by force of gravity from a variable height. U.S. Pat. No. 2,617,293 discloses a Charpy or Izod type of impact test as applied to notched test specimens in the shape of rods or bars, wherein the notch is cylindrical in shape and contains a snugly fitting hard cylindrical core inserted therein.

The most common tests used at present are the "Izod" and "Charpy" methods which are described in detail by The American Society for Testing and Materials under test method ASTM D-256-73. The apparatus employed in these tests consists of a cantilever beam or simple beam pendulum device. Other impact tests which are in use include the so-called tensile impact test and drop weight impact tests.

While the ASTM test methods have met with varying degrees of approval, they all involve a rather elaborate procedure in the preparation of test specimens. For example, test specimens must be of a certain geometry and must be molded in a controlled manner. This usually means that the plastics fabricator must mold or extrude a sufficient quantity of the material, often using production equipment, under precisely controlled processing conditions. This processed material must then be cut or machined into the required geometric shape. For Izod and Charpy, the test specimens must also be precisely notched by machine, which introduces a potentially major source of variation. Next the specimens must be conditioned at about 23° C. and 50% RH for a period of not less than 40 hours. The drop weight impact tests suffer from the deficiency that a large number of specimens are required to obtain a numerical test value, basically because the test is a go or a no-go type, and the criteria for product failure are more difficult to define.

The value of such test methods as a quality control tool is thus somewhat diminished because often small variations in specimen preparation and conditioning from day to day and between different technicians can be a source of error as far as recorded impact resistance is concerned. Also, the large amount of time involved in preparing and conditioning specimens means that the user of the materials must wait for a period of days to verify that a given lot of plastic meets his minimum impact specifications.

Accordingly, it is an object of the present invention to provide a simple and effective method for determining impact properties of relatively stiff materials.

Another object is to provide a method for determining impact properties of plastic materials wherein the preparation of test specimens is greatly simplified.

SUMMARY OF THE INVENTION

These and other objects of the invention may be achieved by a method whereby a test specimen in the form of a thin unnotched strand of known thickness or diameter is fixedly mounted in a holding means and is subjected to an impact by a striking means having a predetermined energy content, said impact applied in a direction substantially perpendicular to the longitudinal axis of said test specimen. The striking means comprises a pendulum-type hammer having a leading striking edge adapted to contact the test specimen at a predetermined distance from the base of the specimen, i.e. the surface point of the holding means in which the specimen is mounted. The energy provided by the striking means is greater than that required to break the specimen. The energy absorbed by the broken specimen is the difference between the potential energy, of the pendulum, and the energy remaining in the pendulum after the break occurs; this is indicated by a pointer and dial mechanism.

The present method embodies the use of a very small quantity of test material in the form of a thin strand which has been shaped by heat extrusion under controlled and repeatable conditions of temperature and pressure. Because of the small quantity of the test material, often in the order of only a few grams, the test material can be cooled or temperature conditioned prior to testing in a very short period of time, e.g., less than one hour. Also, no notching of the test strand is necessary because the concentration of stress required in an impact test is afforded by a fairly narrow tolerance between the striking surface of the hammer and the surface point of the holding means in which the test specimen is mounted.

Impact values for the various materials tested may be readily calculated by a mathematical formula as a function of the diameter of the test specimen at the point of break and the energy required to break it.

DETAILED DESCRIPTION OF THE INVENTION

Figures 1, 2:
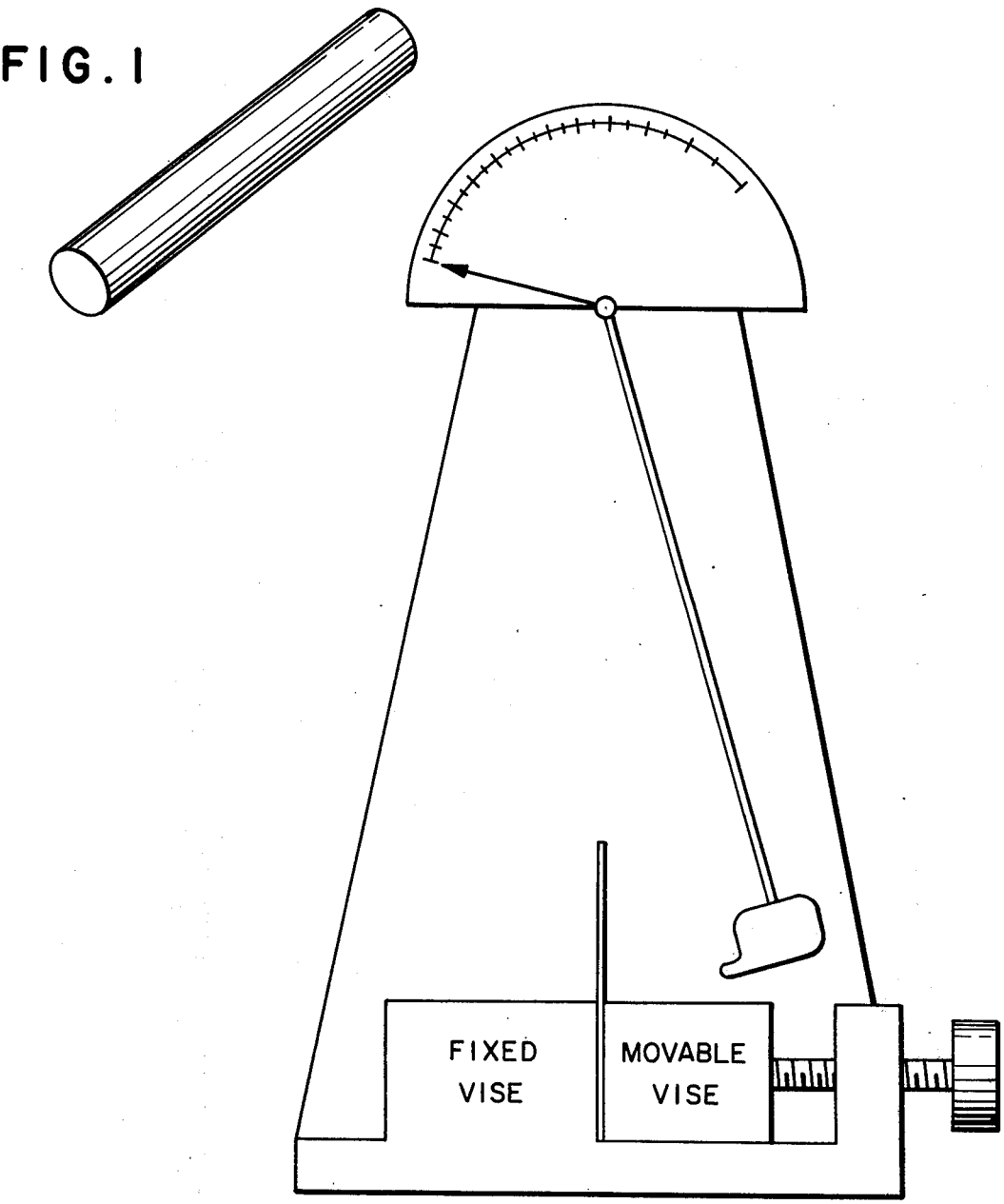
FIG. 1 is a perspective, non-scale view of a cylindrical strand of a test specimen.
FIG. 2 is a schematic diagram of a test specimen mounted in an impact measuring device suitable for carrying out the process of the present invention.

The process according to the present invention is adapted to be performed using a modified cantilever beam impact machine of the type currently in use for performing Izod-type impact tests in accordance with the description of ASTM test D-256-73, which test description is incorporated herein by reference. However, because of the small mass of the test specimen, the amount of energy which must be delivered by the pendulum to break any given sample is considerably less than that required to break a standard Izod sample. Thus, whereas the Izod test requires a basic pendulum energy of 2.00 ± 0.10 ft.-lbs. (section 4.6 of ASTM D-256-73), the present test is readily performed using a pendulum which delivers a basic pendulum energy of 1.77 ± 0.01 inch/lbs, or 0.200 ± 0.01 joules. Additional weights may be added to the pendulum to increase the pendulum energy up to 12.00 inch lbs or more for samples having high impact values and, of course, corresponding scales are provided to correlate scale readings with pendulum energy.

Because of the smaller energy requirements, the other dimensions of the pendulum machine may be less than dimensions specified in ASTM D-256-73. For example, the vertical height of fall of the striking nose may be less than the 24.0 ± 0.1 in. specified in section 4.4, for example, 12.0 ± 0.1 in. The effective length of the pendulum may be less than the range of 12.8 to 16.0 in. specified in Section 4.5, for example 7.0 to 9.0 in., preferably 8.0 in. Because of this decrease in machine dimensions, the velocity of the striking nose at the moment of impact will be less than that obtained with the standard Izod device, and will generally be in the order of about 8 feet per second. Once dimensions of a given apparatus are established, such dimensions should be maintained for all tests in order to obtain meaningful results between the various samples tested.

The striking nose of the pendulum may be as specified in Section 4.3 of ASTM D-256-73, i.e., it may be of hardened steel and have a cylindrical surface having a fixed radius of curvature such as about 0.031 ± 0.005 in. with its axis horizontal and perpendicular to the plane of swing of the pendulum. Those portions of the pendulum adjacent and below the cylindrical striking edge should be recessed or otherwise inclined away from the surface of the vise or holding device in which the test specimen is mounted so that there will be no chance for other than the cylindrical surface coming into contact with test specimen after break.

Of critical importance to the validity and reproducibility of impact tests performed according to the present process is the standardization of the distance between the point on the pendulum striking surface which contacts the test specimen during the swing adjacent the base of the specimen and the proximate top surface of the holding device holding a cantilever mounted test specimen. The distance between these surfaces should be greater than the sum of the thickness of the test specimen and the portion of the cylindrical striking nose below that point on the striking nose which contacts the specimen to allow for free swing through of the pendulum in the event of a hinge break. On the other hand this distance should not be so great that the striking stress is distributed over more than the very smallest longitudinal dimension of the cantilever mounted specimen. Accordingly, where specimens are prepared by techniques wherein the variation in thickness from specimen to specimen is less than the average thickness of all of such specimens, standardization of the distance between the aforementioned surfaces equal to less than twice the average thickness of the test specimens has been established. For specimens prepared by techniques as hereinafter described, the distance is established such that the striking nose shall make initial contact with the specimen on a line located about 0.125 ± 0.002 inches above the top surface of the holding vise.

The holding device in which the test specimen is mounted is adapted to hold the specimen as a vertical cantilever beam with the longitudinal axis of the specimen being perpendicular to the top planar surface of the holding device and to the striking nose of the pendulum hammer. A suitable holding device is a vise having one fixed and one movable jaw. One or both jaws should have a centrally positioned vertical notch of such shape that the notch will serve to seat and anchor the test specimen when the jaws are closed. It has been found that the amount of clamping pressure applied to the various test specimens should be uniform and standardized, and should be at least sufficient to prevent any movement of the specimen during testing. Accordingly the screw shaft of the vise is preferably equipped with a torque/clutch type of device similar to that employed in micrometer caliper measuring instruments.

The pointer and dial mechanism used for measuring the potential energy of the pendulum and the energy extracted from the pendulum in breaking test specimens may be mounted in the pendulum machine as described in ASTM D-256-73, and may be calibrated in inch-pounds, inch-ounces, or directly in joules.

As previously indicated, one of the distinct advantages of the present impact test method is that the preparation of plastic test specimens is greatly simplified as compared with other conventional methods. Small cylindrical linear strands of plastic having a diameter of less than about 0.20 inch, preferably about 0.080 ± 0.035 inch and cut to a length of about 1.0 ± 0.1 inch are ideally suited as test specimens. These strands should contain no air pockets, be of substantially uniform density, and are unnotched, i.e. have a continuous and smooth circumferential surface area. Such specimens may be readily prepared by extruding a heat softened mass of plastic material under standardized conditions of temperature and pressure to obtain thin rods of the plastic, cooling at Standard Laboratory conditions and cutting these rods into a number of one inch long cylinders to obtain a plurality of test specimens. One particularly suitable device for the preparation of specimens is an extrusion plastometer which is commonly used in most laboratories to measure the flow rate of thermoplastics. Using this device the flow rate is measured by heating the plastic above its melting point or softening point to a certain temperature which may vary depending on the type of plastic but which is standardized for a given type of plastic and which is sufficient to form a softened and flowable mass, and vertically extruding the plastic through a cylindrical die using a force applied by means of a gravity fall weighted piston. Such a device and a complete discussion of the temperature, pressure and apparatus specifications involved in carrying out the flow rate test are discussed in ASTM D 1238-73, which test method is incorporated herein by reference. Temperatures and pressures normally employed will vary depending on the softening or melting points of the plastic and its inherent viscosity, but normally temperatures within the range of about 125° to 300° C. and pressures within the range of about 6 to 450 psi are suitable. For most materials, the range will be in the order of about 150° to 250° C. and about 20 to 150 psi respectively. Similar laboratory devices using a constant pressure extrusion force such as a rheology apparatus may also be used for the preparation of specimens so long as the specimens are all prepared using standardized conditions of temperature and pressure.

Plastic rods issuing from the extrusion device should be conditioned under Standard Laboratory Conditions (73.4 ± 3.6° F. and 50 ± 5% RH) for a specific period of time which need not exceed one hour. Because the mass of plastic in these rods is relatively small, the material is properly cooled or temperature conditioned within 30 to 60 minutes after extrusion. Thereafter the rods are cut into suitable lengths for testing.

With respect to set up, adjustment, calibration and correction of the impact machine for such factors as windage, the procedures recited in Appendices A1 and A2 of ASTM D-256-73 may also be applied to the present method where appropriate. Since the present method may measure impact in inch-pounds, or joules, instead of foot/pounds, and since the size of the test specimen is small as compared with a Standard Izod or Charpy sample, it is important that all calibrations and adjustments be carefully performed. It is also important that the bearings about which the pendulum arm swings be designed so as to provide a minimum amount of bearing friction or drag. A suitable machine which may be modified for satisfactory performance of the present impact test is the model CS-183T1 Mini-Max impact tester marketed by Custom Scientific Instruments, Inc., of Whippany, New Jersey.

DESCRIPTION OF THE PREFERRED EMBODIMENT

Following is a description of the preferred mode for conducting impact tests on various samples of plastics including general purpose polystyrene, high impact polystyrene (HIPS) and ABS resins. The impact machine used for these tests was Model C 183 T1 manufactured by Custom Scientific Instruments, Inc., which machine was equipped with a measuring scale having three sets of graduations, namely 1.5, 3.0 and 6.0 inch-pounds to coincide with weights adapted to be affixed to the pendulum hammer. The machine was equipped with a vise having a flat top planar surface and a vertical notch centrally positioned in the jaws for holding a cylindrical strand of test material. The screw mechanism on the vise was equipped with a clutch mechanism to insure constant locking pressure when the moveable jaw is closed on the test specimen. The location of the test specimen with respect to the pendulum hammer was such that when the pendulum is free hanging, the hammer striking surface was within 0.5 percent of a scale unit of touching the front face of the specimen. The vise notch length was such that approximately ½ inch length of the test specimen was positioned below the top surface of the vise. The tolerance between the top planar surface of the vise and the striking surface of the hammer which contacts the specimen was set at about 0.125 inches. The machine was equipped to provide a basic pendulum energy of 3 inch-pounds.

Test specimens were prepared using a flow plastometer equipped with a heater, weighted extrusion piston and a circular extrusion die having a diameter of about 0.0825 inch. The conditions for extruding test specimen were as stated in ASTM D 1238-73. In the case of polystyrene, HIPS and ABS resins, the plastometer was adjusted to Standard Test Conditions of temperature and load of 200° C. and 5,000 g. respectively such that the approximate extrusion pressure was about 100 psi.

Samples were extruded in the shape of thin rods under Standard Laboratory Conditions. These now solid rods were cut in lengths of about six inches and conditioned by storage at the Standard Laboratory Conditions of 73° F. and 50% RH for about 30 minutes. The rods were then cut into one inch lengths for testing.

Prior to testing the impact machine was adjusted, calibrated and corrected as provided in ASTM D-256-73.

Test specimens were fixedly mounted in the holding vise such that approximately ½ inch of length was below the top surface of the vise and correspondingly about ½ inch of length was above. The diameter of the specimen was then carefully measured to the nearest thousandth of an inch at the point of anticipated break, adjacent to the top surface of the vise, using a caliper; and the average of five such readings was assigned as the specimen diameter at the point of break.

The pendulum was then released from the hold position and the energy in inch-pounds to break was taken from the scale reading to the nearest hundredths.

This procedure was repeated on different test specimens of the same plastic material until a total of five complete or hinge breaks of the specimens were obtained. It was found that the diameter of the different specimens was within the range of about 0.090 ± 0.020 inch and that the scale readings varied as a function of the diameter of the specimen; however, such variation was not linear. Accordingly, it was not meaningful to report direct readings from the scale as impact values. Mathematical calculations have indicated that a substantially linear relationship between specimen diameter at the point of break and scale reading according to the present method is established by the following formula:

$$\frac{R}{D^3} = K$$

wherein:
D = average specimen diameter
R = scale reading
K = Kravitz impact value.

Thus a sample having a diameter of 0.085 inch and an energy to break of 1.23 inch-pounds would have a Kravitz Impact value of about 2003.

Using the above test apparatus and method, a series of experimental round-robin tests were performed by a number of different laboratories and operators to verify the validity of the method and also to establish the reproducability and precision of data generated using this method as compared with the commonly used notched Izod method. Plastic specimens used in these tests were prepared from control samples of three different plastics, i.e., general purpose polystyrene, high impact polystyrene and ABS resin. Izod tests were performed by the method outlines in ASTM D-256-73. Results are shown in Table 1.

TABLE 1

| | Polystyrene | | HIPS | | ABS | |
|---|---|---|---|---|---|---|
| | I (ft.lbs) | K | I (ft.lbs.) | K | I (ft.lbs) | K |
| LAB 1 | .32 | 207 | 2.30 | 2006 | 7.60 | 2737 |
| LAB 2 | .40 | 160 | 2.30 | 2056 | 7.20 | 2857 |
| LAB 3 | .28 | 164 | 2.23 | 1970 | 6.68 | 2853 |
| LAB 4 | .32 | 201 | 2.30 | 1903 | 6.27 | 2796 |
| LAB 5 | .25 | 181 | 2.00 | 1900 | 6.27 | 2707 |
| LAB 6 | .24 | 168 | 2.25 | 2007 | 7.31 | 2705 |

TABLE 1-continued

|  | Polystyrene | | HIPS | | ABS | |
| --- | --- | --- | --- | --- | --- | --- |
|  | I (ft.lbs) | K | I (ft.lbs.) | K | I (ft.lbs) | K |
| LAB 7 | .22 | NA | 2.18 | NA | 6.80 | NA |
| Ave. | .29 | 180 | 2.22 | 1974 | 6.88 | 2776 |
| Std. Dev. | .06 | 20 | 0.11 | 62 | 0.52 | 70 |
| C.O.V. | 21% | 11.1% | 4.9% | 3.1% | 7.5% | 2.5% |

As can be seen from the table, the present method (K) is much more precise than the Izod (I) method and shows a much lower coefficient of variation (COV) for each of the plastic types evaluated. Thus, the present method permits evaluation of the impact properties of a given plastic material in a quick and simple manner.

Although the present invention has been described in the preferred embodiment using non-metric system measurements, it should be emphasized that the method can also be carried out employing metric measurements, and thus the energy extracted in breaking specimens can be reported in inch-ounces, inch-pounds, mm. or cm.-grams, or directly in joules. The reported K value as calculated using the above mathematical formula should reflect the measuring system used in conducting the test, such as by reporting K in terms of inch-pounds per cubic inch, centimeter-grams per cubic centimeter, or joules per cubic centimeter.

While the invention has been described with reference to the structure disclosed herein, it is not confined to the specific embodiment set forth, and this application is intended to cover such operative modifications or changes as may come within the scope of the following claims.

What I claim is:

1. A method for determining the impact properties of a stiff plastic material comprising the steps of:
   a. providing a cylindrical strand of solid plastic having a substantially uniform density and having a smooth continuous circumferential surface area;
   b. providing an impact measuring device comprising a specimen holding means, a free swinging pendulum of known energy content having a specimen striking surface, and scale means for measuring the energy extracted from said pendulum;
   c. fixedly mounting said strand in said holding means such that a portion of said strand is in the path of said specimen striking surface and substantially perpendicular thereto when said pendulum is allowed to swing, the base of said strand adjacent and above the top planar surface of said specimen holding means being of predetermined diameter;
   d. producing an impact against the side of said strand at a point adjacent its base, said impact being substantially perpendicular to the longitudinal axis of said strand; and
   e. determining the excess energy remaining in said pendulum after breaking said strand.

2. The method of claim 1 wherein the distance between the point on said strand struck by said pendulum striking surface and the top planar of said holding means at the base of said strand is less than about twice the diameter of said strand.

3. The method of claim 2 wherein said distance is about 0.125 inches.

4. The method of claim 1 wherein the predetermined diameter of said strand base is within the range of about 0.080 ± 0.035 inch.

5. The method of claim 1 wherein the energy content of said free swinging pendulum is within the range of about 1.5 to 12 inch-pounds.

6. The method of claim 1 wherein said specimen holding means comprises a vise having one fixed and one movable jaw, at least one of said jaws being notched to seat said strand in a substantially vertical position such that a portion of said strand extends above the top planar surface of said vise.

7. A method for determining the impact properties of a stiff plastic material comprising the steps of:
   a. passing a heat softened mass of said plastic material vertically downward through a cylindrical die to form a strand of plastic material having a substantially uniform density and a smooth continuous circumferential surface area;
   b. Cooling and conditioning said strand under Standard Laboratory Conditions for a period of at least about 30 minutes;
   c. providing an impact measuring device comprising a specimen holding means, a free swinging pendulum of known energy content having a specimen striking surface, and scale means for measuring the energy extracted from said pendulum;
   d. fixedly mounting said strand in said holding means such that a portion of said strand is in the path of said specimen striking surface and substantially perpendicular thereto when said pendulum is allowed to swing, the base of said strand adjacent and above the top planar surface of said specimen holding means being of predetermined diameter;
   e. producing an impact against the side of said strand at a point adjacent its base, said impact being substantially perpendicular to the longitudinal axis of said strand; and
   f. determining the excess energy remaining in said pendulum after breaking said strand.

8. The method of claim 7 wherein the predetermined diameter of said strand base is within the range of about 0.080 ± 0.035 inch.

9. The method of claim 8 wherein the distance between the point on said strand struck by said pendulum striking surface and the top planar surface of said holding means at the base of said strand is about 0.125 inches.

* * * * *